(12) United States Patent
Kim et al.

(10) Patent No.: US 6,251,427 B1
(45) Date of Patent: Jun. 26, 2001

(54) PHARMACEUTICAL CAPSULE COMPOSITIONS CONTAINING LORATADINE AND PSUEDOEPHEDRINE

(75) Inventors: Hyun-Soo Kim; Young-Joon Park, both of Kyonggi-do; Hang-Bum Jo, Suwon-si, all of (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 09/507,995

(22) Filed: Feb. 22, 2000

(30) Foreign Application Priority Data

Feb. 23, 1999 (KR) .............................. 99-0005873

(51) Int. Cl.[7] .............................. A61K 9/48; A61K 9/52; A61K 9/54
(52) U.S. Cl. .................. 424/451; 424/452; 424/457; 424/458
(58) Field of Search ..................... 424/480, 458, 424/469, 451, 457, 452

(56) References Cited

U.S. PATENT DOCUMENTS 5,314,697 * 5/1994 Kwan et al. ..................... 424/480
5,840,329 * 11/1998 Bai ....................................... 424/458

FOREIGN PATENT DOCUMENTS 96-6917   3/1996   (KR) .

* cited by examiner

*Primary Examiner*—Thurman K. Page
*Assistant Examiner*—Blessing Fubara
(74) *Attorney, Agent, or Firm*—Rosenman & Colin, LLP

(57) ABSTRACT

A pharmaceutical capsule composition for oral administration exhibiting controllable, satisfactory release profiles of both loratadine and pseudoephedrine or its salts, which comprises: (a) a plurality of rapid-release pellets (pellets A), each pellet containing (i) a therapeutically effective amount of loratadine, (ii) pseudoephedrine or a pharmaceutically acceptable salt thereof, and (iii) one or more pharmaceutically acceptable excipients; and (b) a plurality of extended-release pellets (pellets B), each pellet containing (i) pseudoephedrine or a pharmaceutically acceptable salt thereof and (ii) one or more pharmaceutically acceptable excipients, which are coated with a water-insoluble polymer in an amount ranging from 2 to 30 wt % and a wet-blocking agent selected from the group consisting of magnesium stearate, talc, fatty acid ester and a mixture thereof in an amount ranging from 2 to 30 wt %, based on the total weight of pellets B.

3 Claims, No Drawings

PHARMACEUTICAL CAPSULE COMPOSITIONS CONTAINING LORATADINE AND PSUEDOEPHEDRINE

FIELD OF THE INVENTION

The present invention relates to a pharmaceutical capsule composition containing loratadine and pseudoephedrine, and more particularly, to a pharmaceutical capsule composition for oral administration, which comprises rapid-release pellets (pellets A) containing loratadine and pseudoephedrine or a pharmaceutically acceptable salt thereof and extended-release pellets (pellets B) containing pseudoephedrine or a pharmaceutically acceptable salt thereof, wherein the pellets B are coated with a water-insoluble polymer and a wet-blocking agent.

BACKGROUND OF THE INVENTION

Pseudoephedrine or a pharmaceutically acceptable salt thereof, e.g., pseudoephedrine sulfate, has been recognized by those skilled in the art as a sympathomimetic drug effective for treating nasal congestion. Loratadine, a non-sedating antihistaminic agent, is also known to be useful as an anti-allergy agent for the treatment of seasonal allergic rhinitis symptoms such as sneezing and itching. Therefore, an oral dosage composition containing both loratadine and pseudoephedrine or a pharmaceutically acceptable salt thereof is useful for treating patients showing the sign and symptoms associated with upper respiratory diseases and allergic rhinitis (see U.S. Pat. No. 5,314,697)

However, the biological half-life of pseudoephedrine sulfate is only about 6.3 hours, while loratadine, which combines with plasma proteins after being absorbed through the gastrointestinal tract, has a much longer biological half life of 12 to 15 hours. Further, loratadine has a poor water-solubility and exhibits a very low dissolution rate. Therefore, a conventional formulation prepared by simply mixing loratadine and pseudoephedrine or its salts is not capable of maintaining therapeutically effective blood concentrations of both ingredients at the same time for a prescribed period.

In order to solve the above problem, U.S. Pat. No. 5,314,697 suggests a film-coated tablet comprising an extended-release matrix core containing pseudoephedrine sulfate and a hydrophilic gel, a coating layer containing loratadine being formed on said core. When this formulation is ingested, loratadine having a longer biological half-life is released from the coating layer before the dissolution of pseudoephedrine sulfate having a shorter biological half-life from the extended-release matrix core.

However, the solubility and dissolution rate of loratadine from the outer layer decrease markedly in a high pH environment, and for this reason, the dissolution of pseudoephedrine sulfate from the extended-release matrix core may be unduly delayed. That is, the dissolution of pseudoephedrine sulfate is highly affected by the degree of wetting and dissolution of loratadine in the outer layer, and therefore, the release profile of pseudoephedrine sulfate fluctuates in an unpredictable manner with the pH of the gastrointestinal fluid which varies widely depending on various factors such as the amount and kind of ingested food.

Further, U.S. Pat. No. 5,807,579 discloses a tablet composition comprising extended-release pellets containing pseudoephedrine or its salts that are dispersed in a matrix containing an antihistaminic agent and optional pseudoephedrine or its salts. However, this composition also suffers from the problem of poor wetting of loratadine at a high pH condition, which may lead to an unsatisfactory mode of pseudoephedrine delivery.

The present inventors have carried out extensive research to solve the aforementioned problems; and, have discovered that a pharmaceutical capsule composition, which comprises rapid-release pellets containing loratadine and pseudoephedrine or a salt thereof, and extended-release pellets containing pseudoephedrine or a salt thereof, which are coated with a water-insoluble polymer and a wet-blocking agent, are free of above problems and exhibit controllable, satisfactory release profiles of both ingredients.

SUMMARY OF THE INVENTION

Accordingly, it is an object of the present invention to provide an improved pharmaceutical capsule composition for oral administration containing loratadine and pseudoephedrine or a pharmaceutically acceptable salt thereof.

In accordance with the present invention, there is provided a pharmaceutical capsule composition for oral administration, which comprises:

(a) a plurality of rapid-release pellets (pellets A), each pellet containing (i) a therapeutically effective amount of loratadine, (ii) pseudoephedrine or a pharmaceutically acceptable salt thereof, and (iii) one or more pharmaceutically acceptable excipients; and (b) a plurality of extended-release pellets (pellets B), each pellet containing (i) pseudoephedrine or a pharmaceutically acceptable salt thereof and (ii) one or more pharmaceutically acceptable excipients, which are coated with a water-insoluble polymer in an amount ranging from 2 to 30 wt % and a wet-blocking agent selected from the group consisting of magnesium stearate, talc, fatty acid ester and a mixture thereof in an amount ranging from 2 to 30 wt %, based on the total weight of pellets B.

DETAILED DESCRIPTION OF THE INVENTION

As used herein, the term "pellets" means pharmaceutical-containing particles having a diameter ranging from about 300 to 1500 microns. The term "rapid-release" refers to a property of the pharmaceutical composition wherein the entire dose of active medicament becomes bioavailable without substantial delay. The term "extended-release" is as expressed in the U.S. Pharmacopoeia (USPXXIV, 1999) and refers to a property of the pharmaceutical composition wherein the contained active medicament becomes bioavailable over an extended period of time after being ingested.

As used herein, the term "therapeutically effective amount" of loratadine and pseudoephedrine refers to the amount required to produce the desired therapeutic response upon the oral administration and can be readily determined by one skilled in the art. In determining the therapeutically effective amount, a number of factors are considered, but not limited to: the bioavailability characteristics of the pharmaceutical composition administered, the dose regimen selected, and other relevant circumstances. For example, the effective doses of loratadine and pseudoephedrine sulfate may be 10 mg and 240 mg per day, respectively. Further, in case of a twice-a-day unit dosage form, the amounts of loratadine and pseudoephedrine sulfate may be 5 mg and 120 mg, respectively.

The rapid-release pellets (pellets A) of the pharmaceutical capsule composition according to the present invention contain a therapeutically effective amount of loratadine, pseudoephedrine or a pharmaceutically acceptable salt thereof, and one or more pharmaceutically acceptable excipients. When the composition of the present invention is administered, the highly water-soluble pseudoephedrine or its salt is readily leached out from the rapid-release pellets upon which the pellets are disintegrated to release loratadine particles to the aqueous gastric environment, thereby enhancing the dissolution rate of loratadine, while a therapeutically effective blood level of pseudoephedrine or its salts is attained rapidly from the beginning.

Pellets A contain pseudoephedrine or its salt in an amount sufficient to produce a therapeutically effective initial concentration of pseudoephedrine and that amount may range from 5 to 50 wt % based on the total amount of pseudoephedrine or its salt in pellets A and B.

The rapid-release pellets of the pharmaceutical composition according to the present invention may contain one or more pharmaceutically acceptable excipients, including a disintegrant, a binder, or a lubricant.

Suitable disintegrants, which may be used to improve the dissolution rate of loratadine, include microcrystalline cellulose, low-substituted hydroxypropyl cellulose (USPXXIV, 1999), sucrose, crospovidone, sodium starch glycolate, and mixtures thereof. Among the disintegrants, preferred are crospovidone, low-substituted hydroxypropyl cellulose and a mixture thereof. The disintegrants may be used in an amount ranging from about 5 to about 50 wt %, preferably from 10 to 30 wt % based on the weight of the rapid-release pellets to produce a satisfactory dissolution profile of loratadine.

The rapid-release pellets may also contain one or more conventional excipients such as binders(e.g., polyvinylpyrrolidone, hydroxypropyl cellulose, gelatin, and the like); and lubricants(e.g., colloidal silicon dioxide, silicon dioxide, talc, and the like).

The rapid-release pellets can be prepared according to the well known methods in the art, i.e. the extrusion & spheronizing method (see *Pharmaceutical Pelletization Technology*, 1989, p187~216), the solution & suspension layering method (see *Drug Dev. Ind. Pharm.*, 1989, 15(8), p1137~1159) and the dry powder layering method (see *Pharmaceutical Pelletization Technology*, 1989, p187~216).

For example, in case the rapid-release pellets are prepared by the dry powder layering method, while a binder solution is sprayed onto an inert carrier, such as crystalline sucrose seeds and microcrystalline cellulose seeds(e.g., Celphere®, Asahi Chemical Co.), in a centrifugal granulator, a mixed powder of loratadine, pseudoephedrine or its salts and pharmaceutical excipients is dusted onto the inert carrier to give the rapid-release pellets of the present invention.

The extended-release pellets (pellets B) of the pharmaceutical capsule composition of the present invention contain pseudoephedrine or a pharmaceutically acceptable salt thereof and one or more pharmaceutically acceptable excipients and are coated with a water-insoluble polymer in an amount ranging from 2 to 30 wt % based on the total weight of the pellets B and a wet-blocking agent selected from the group consisting of magnesium stearate, talc, fatty acid ester and a mixture thereof in an amount ranging from 2 to 30 wt % based on the total weight of the pellets B.

The dissolution of pseudoephedrine from the extended-release pellets is not affected by the dissolution of loratadine, and thus, a desired release profile of this active ingredient can be obtained.

The extended-release pellets, i.e., pellets B may be prepared by coating core pellets containing pseudoephedrine or its salt with a water-insoluble polymer and a wet-blocking agent or by dispersing pseudoephedrine or its salt into a water-insoluble polymer matrix containing a wet-blocking agent.

In case that the pseudoephedrine-containing core pellet is coated with the water insoluble polymer and a wet blocking agent to form a coating layer on the core pellet, the constitution and/or thickness of the coating layer of pellets B can be easily controlled, thereby obtaining a desired dissolution profile (sigmoidal dissolution profile) of pseudoephedrine which does not depend on the pH of the gastrointestinal fluid. Therefore, coating type pellets are preferably used as an extended release pellets of the inventive composition.

Suitable water-insoluble polymers, which may be used in the present invention, may be selected from the group consisting of ethyl cellulose, methacrylic acid copolymer (e.g., Eudragit L, Eudragit RS, Eudragit RL, and Eudragit S), a hydrogenated caster oil, shellac, and a mixture thereof.

The core pellets of the extended-release pellets can be prepared according to well known methods in the art, i.e. the extrusion & spheronizing method (see *Pharmaceutical Pelletization Technology*, 1989, p187~216), the solution & suspension layering method (see *Drug Dev. Ind. Pharm.*, 1989, 15(8), p1137~1159) and the dry powder layering method (see *Pharmaceutical Pelletization Technology*, 1989, p187~216).

For example, in accordance with the dry powder layering method, while a binder solution is sprayed onto an inert carrier, such as such as crystalline sucrose seeds and microcrystalline cellulose seeds(e.g., Celphere®, Asahi Chemical Co.), in a centrifugal granulator, a mixed powder of pseudoephedrine or its salt and pharmaceutical excipients is dusted onto the inert carrier to give the core pellets of the extended-release pellets of the present invention. Then, the core pellets are coated with a solution containing a water-insoluble polymer and a wet-blocking agent in an appropriate solvent to afford the extended-release pellets of the present invention. Suitable solvents, which may be used in the present invention, include acetone, ethanol, isopropyl alcohol, methylene chloride and the mixture thereof.

Pharmaceutical excipients which may be used in preparing the extended release pellets of the present invention include one or more conventional excipients known in the art, for example, plasticizers such as polyethylene glycol 6000, diethyl phthalate, and dibutyl sebacate; diluents such as microcrystalline cellulose and sucrose; disintegrants such as low-substituted hydroxypropyl cellulose, crospovidone, sodium starch glycolate, and a mixture thereof; binders such as polyvinylpyrrolidone, hydroxypropyl cellulose, and gelatin; and lubricants such as colloidal silicone dioxide, silicone dioxide, magnesium stearate, and talc.

The pharmaceutical capsule composition of the present invention can be readily formulated into a capsule form by filling the aforementioned rapid-release pellets and extended-release pellets into an appropriate capsule.

When the capsule composition of the present invention is orally administered, loratadine is readily released at a higher rate from the capsule composition than from a conventional tablet composition.

Further, pseudoephedrine or its salt having a shorter biological half-life than loratadine is dissolved out first from the rapid-release pellets and then from the extended-release pellets for immediate and extended dissolution delivery of pseudoephedrine. The extended-release pellets are coated with a water-insoluble polymer to give an effective extended-release activity. Especially, the coating layer of the extended-release pellets has a wet-blocking agent, thereby affording pseudo-multiple dissolution profile.

Therefore, the pharmaceutical capsule composition of the present invention shows prompt and long-acting effects when administered, independently of various factors associated with gastrointestinal environment.

The following Examples and Test Examples are given for the purpose of illustration only, and are not intended to limit the scope of the invention.

EXAMPLE 1

Preparation of Rapid-Release Pellets Containing Loratadine and Pseudoephedrine Sulfate A binder solution was prepared by dissolving 5.0 g of polyvinylpyrrolidone in 120 g of water. 25 g of loratadine, 180 g of pseudoephedrine sulfate, 25 g of microcrystalline cellulose, 75 g of low substituted hydroxypropyl cellulose, 75 g of crospovidone and 1.5 g of colloidal silicon dioxide were mixed and screened through a 20-mesh sieve to give a mixed powder. While the binder solution prepared above was sprayed onto 250 g of crystalline sugar seeds in a centrifugal granulator, the mixed powder was dusted onto the crystalline sugar seeds in the centrifugal granulator to afford pellets. (the rotation panel rate: 140–200 rpm, the spraying rate of the binder solution: 2–20 ml/min, air spraying pressure: 1–2 kg/cm$^2$, air spraying volume: 5–300 L/min, powder spraying rate: 5–30 g/min)

EXAMPLES 2 AND 3

Preparation of Rapid-Release Pellets Containing Loratadine and Pseudoephedrine Sulfate The procedure of Example 1 was repeated except that the amounts of the components were varied as shown in Table 1 to obtain additional samples of rapid-release pellets containing both pseudoephedrine sulfate and loratadine.

TABLE 1

| | | Example 2 | Example 3 |
|---|---|---|---|
| Active ingredients | Loratadine | 25 g | 25 g |
| | Pseudoephedrine sulfate | 240 g | 270 g |
| Diluents | Microcrystalline cellulose | 25 g | 25 g |
| Disintegrants | Low substituted hydroxypropyl cellulose | 75 g | 50 g |
| | Crospovidone | 75 g | 50 g |
| Lubricants | Colloidal silicon dioxide | 1.5 g | 1.5 g |
| Binder | Polyvinylpyrrolidon | 5.0 g | 5.0 g |
| Inert carrier | Crystalline sugar seed | 250 g | 250 g |

EXAMPLE 4

Preparation of Core Pellets Containing Pseudoephedrine Sulfate

A binder solution was prepared by dissolving 20 g of hydroxypropyl cellulose in 480 g of water. 1200 g of pseudoephedrine sulfate and 3 g of colloidal silicon dioxide were mixed and screened through a 20-mesh sieve to give a mixed powder. While the binder solution prepared above was sprayed onto 600 g of crystalline sugar seeds in a centrifugal granulator, the mixed powder was dusted onto the crystalline sugar seeds in the centrifugal granulator to afford pellets. The obtained pellets were dried at 50° C. until the water content thereof, measured with Kett-moisture analyzer, became less than below 2% to give core pellets containing pseudoephedrine sulfate.

EXAMPLES 5 AND 6

Preparation of Core Pellets Containing Pseudoephedrine Sulfate

The procedure of Example 4 was repeated except that the amounts of the components were varied as shown in Table 2 to obtain additional samples of core pellets containing pseudoephedrine sulfate.

TABLE 2

| | | Example 5 | Example 6 |
|---|---|---|---|
| Active ingredients | Pseudoephedrine sulfate | 1200 g | 1200 g |
| Binders | Hydroxypropyl cellulose | — | 20 g |
| | Polyvinylpyrrolidon | 20 g | — |
| Lubricants | Colloidal silicon dioxide | 3 g | 3 g |
| | Magnesium stearate | — | 240 g |
| Inert carriers | Crystalline sugar seed | 600 g | 600 g |

EXAMPLES 7 TO 10

Preparation of Extended-Release Pellets Containing Pseudoephedrine Sulfate

Using the core pellets prepared in Example 4 and the materials shown in Table 3, extended-release pellets containing pseudoephedrine sulfate were prepared by the following procedure.

A suspension of the water-insoluble polymer, magnesium stearate and other ingredients in a mixture of acetone and isopropyl alcohol was sprayed onto the core pellets containing pseudoephedrine sulfate in a centrifugal-360 granulator, and then dried at 50° C. until the water contents dropped below 2% to give extended-release pellets containing pseudoephedrine sulfate.

EXAMPLE 11

Preparation of Extended-Release Pellets Containing Pseudoephedrine Sulfate

The procedure of Examples 7–10 was repeated to obtain extended-release pellets containing pseudoephedrine sulfate by using the core pellets obtained in Example 6 and the materials shown in Table 3.

TABLE 3

| | Ex. 7 | Ex. 8 | Ex. 9 | Ex. 10 | Ex. 11 |
|---|---|---|---|---|---|
| Pseudoephedrine sulfate core pellets | 280 | 280 | 280 | 280 | 280 |
| Ethyl cellulose | 15 | 30 | — | 26 | 15 |
| Eudragit RS | — | — | 40 | 13 | — |
| Diethyl phthalate | 1.5 | 3.0 | 4.0 | 3.9 | 1.5 |
| Magnesium stearate | 18 | — | — | 13 | — |
| Talc | — | 10 | 10 | — | — |
| Acetone | 150 | 300 | 400 | 390 | 150 |
| Isopropyl alcohol | 150 | 300 | 400 | 390 | 150 |

EXAMPLES 12 TO 15

Preparation of Capsules 127.3 g, 139.3 g, and 135.3 g of the rapid-release pellets prepared in Examples 1, 2, and 3 were respectively mixed with 143.3 g, 122.9 g, and 112.6 g of the extended-release pellets prepared in Example 7 to afford three batches of mixed pellets which were filled into No.1 capsule to give the capsules of Examples 12, 13, and 14, respectively. And also, 127.3 g of the rapid-release pellets prepared in Example 1 were mixed with 153.1 g of the extended-release pellets prepared in Example 10 to obtain a pellet mixture, which was filled into No.1 capsule to give the capsule of Example 15. The amounts of the ingredients present in each capsule are same as in Table 4.

TABLE 4

|  | Ex. 12 (Ex. 1 + 7) | Ex. 13 (Ex. 2 + 7) | Ex. 14 (Ex. 3 + 7) | Ex. 15 (Ex. 1 + 10) |
|---|---|---|---|---|
| Loratadine | 5 | 5 | 5 | 5 |
| Pseudoephedrine sulfate |  |  |  |  |
| Rapid-release pellet | 36 | 48 | 54 | 36 |
| Extended-release pellet | 84 | 72 | 66 | 84 |
| Microcrystalline cellulose | 5 | 8.6 | 8.6 | 8.6 |
| Low substituted hydroxypropyl cellulose | 15 | 15 | 15 | 15 |
| Crospovidone | 15 | 15 | 15 | 15 |
| Colloidal silicon dioxide | 0.5 | 0.48 | 0.47 | 0.5 |
| Hydroxypropyl cellulose | 1.4 | 1.2 | 1.1 | 1.4 |
| Polyvinylpyrrolidon | 1 | 1 | 1 | 1 |
| Ethyl cellulose | 7.5 | 15 | — | 13 |
| Eudragit RS | — | — | 20 | 6.5 |
| Diethyl phthalate | 0.75 | 1.5 | 2.0 | 3.9 |
| Magnesium stearate | 9 | — | — | 6.5 |
| Talc | — | 5 | 5 | — |

TEST EXAMPLE 1

Dissolution Test (1)

A measured amount of each of the extended-release pellets prepared in Example 7–11 was filled into a basket, and subjected to a dissolution test under the following conditions. The results are shown in Table 5.

Dissolution Test Condition:

Test Solution: 0.1N Hydrochloric acid 900 ml

Temperature: 37±0.5° C.

Method: Basket Method (U.S. Pharmacopoeia)

TABLE 5

| Dissolution (%) of pseudoephedrine sulfate | | | | |
|---|---|---|---|---|
|  | 1 hour | 2 hours | 4 hours | 6 hours |
| Ex. 7 | 15.5 | 25.5 | 64.1 | 82.6 |
| Ex. 8 | 21.5 | 41.9 | 63.3 | 84.6 |
| Ex. 9 | 15.5 | 37.8 | 58.2 | 78.6 |
| Ex. 10 | 19.7 | 45.4 | 66.9 | 88.4 |
| Ex. 11 | 15.5 | 52.1 | 65.6 | 79.0 |

As shown in Table 5, the extended-release pellets of the present invention exhibit in each case, a satisfactory dissolution profile of pseudoephedrine sulfate over a period of more than 6 hours.

TEST EXAMPLE 2

Dissolution Test (2)

A measured amount of each of the capsules prepared in Examples 12–15 was filled into a basket, and then subjected to a dissolution test under the following conditions. The same amount of Clarinase (Shering plough, USA) was also filled into the basket and subjected to the test. The results are shown in Tables 6 and 7.

Dissolution Test Condition:

Test Solution:
0.1N Hydrochloric acid 900 ml
pH4.0 acetate buffer 900 ml
pH6.8 phosphate buffer 900 ml Temperature: 37±0.5° C.

Method: Basket Method (U.S. Pharmacopoeia)

TABLE 6

| Dissolution (%) of loratadine for 1 hour | | | | | |
|---|---|---|---|---|---|
| pH | Clarinase | Ex. 12 | Ex. 13 | Ex. 14 | Ex. 15 |
| 1.0 | 88.5 | 91.7 | 94.5 | 97.2 | 95.3 |
| 4.0 | 53.4 | 51.5 | 52.9 | 55.1 | 54.1 |
| 6.8 | 0 | 10.2 | 10.9 | 12.1 | 9.7 |

TABLE 7

| Dissolution (%) of pseudoephedrine sulfate | | | | | |
|---|---|---|---|---|---|
| pH |  | 1 hour | 2 hours | 4 hours | 6 hours |
| 1.0 | Clarinase | 48.8 | 49.0 | n.m. | 82.6 |
|  | Ex. 12 | 40.9 | 47.9 | 74.8 | 87.8 |
|  | Ex. 13 | 49.3 | 55.3 | 78.4 | 89.6 |
|  | Ex. 14 | 53.5 | 59.0 | 80.2 | 90.4 |
|  | Ex. 15 | 43.8 | 61.8 | 76.8 | 91.9 |
| 4.0 | Clarinase | 47.4 | 47.8 | n.m. | 50.1 |
|  | Ex. 12 | 39.1 | 49.1 | n.m. | 84.9 |
|  | Ex. 13 | 48.4 | 55.1 | n.m. | 87.9 |
|  | Ex. 14 | 51.3 | 57.9 | n.m. | 88.5 |
|  | Ex. 15 | 44.3 | 60.9 | n.m. | 92.7 |
| 6.8 | Clarinase | 44.1 | 48.1 | n.m. | 49.7 |
|  | Ex. 12 | 40.8 | 52.3 | n.m. | 85.1 |
|  | Ex. 13 | 50.1 | 57.1 | n.m. | 89.9 |
|  | Ex. 14 | 52.7 | 59.1 | n.m. | 87.9 |
|  | Ex. 15 | 46.2 | 63.7 | n.m. | 93.1 |

* N.M.: Not measured

As shown in Table 6, loratadine was rapidly released from each of the tested compositions at pH 1.0. However, at pH 4.0 and 6.8, the dissolution of loratadine from Clarinase was completely suppressed.

As shown in Table 7, at pH 1.0, the dissolution rate of pseudoephedrine sulfate was not significantly different among the compositions examined.

However, at pH 4.0 or 6.8, the amount of pseudoephedrine sulfate released from Clarinase remained low at about 50% throughout the test period of 6 hours. This suggests that loratadine which remains undissolved under a high pH condition blocks the dissolution of pseudoephedrine. In sharp contrast, the dissolution of pseudoephedrine sulfate from the composition of the present invention is not influenced by pH, the release profile being the same over a pH range of 1.0 to 6.8.

Also, the fact that dissolution profile of pseudoephedrine sulfate from the composition of the present invention exhibits a sigmoidal curve is particularly advantageous to afford pseudo-multiple administration of pseudoephedrine sulfate.

While the embodiments of the subject invention have been described and illustrated, it is obvious that various changes and modifications can be made therein without departing from the spirit of the present invention which should be limited only by the scope of the appended claims.

What is claimed is:

1. A pharmaceutical capsule composition for oral administration, which comprises:
    (a) a plurality of rapid-release pellets (pellets A), each pellet containing (i) a therapeutically effective amount of loratadine, (ii) pseudoephedrine or a pharmaceutically acceptable salt thereof, and (iii) one or more pharmaceutically acceptable excipients; and
    (b) a plurality of extended-release pellets (pellets B), each pellet containing (i) pseudoephedrine or a pharmaceutically acceptable salt thereof and (ii) one or more pharmaceutically acceptable excipients, which are coated with a water-insoluble polymer in an amount ranging from 2 to 30 wt % and a wet-blocking agent selected from the group consisting of magnesium stearate, talc, fatty acid ester and a mixture thereof in an amount ranging from 2 to 30 wt %, based on the total weight of pellets B.

2. The capsule composition of claim 1, wherein the amount of pseudoephedrine or a pharmaceutically acceptable salt thereof contained in pellets A ranges from 5 to 50 wt % based on the total amount of pseudoephedrine or its salt present in the capsule.

3. The capsule composition of claim 1 or 2, wherein the water-insoluble polymer is selected from the group consisting of ethyl cellulose, methacrylic acid copolymer, a hydrogenated caster oil, shellac, and a mixture thereof.

* * * * *